United States Patent
Su et al.

(10) Patent No.: US 11,393,434 B2
(45) Date of Patent: Jul. 19, 2022

(54) METHOD, PROCESSING DEVICE, AND DISPLAY SYSTEM FOR INFORMATION DISPLAY

(71) Applicant: Industrial Technology Research Institute, Hsinchu (TW)

(72) Inventors: Yu-Hsuan Su, Kaohsiung (TW); Tzu-Yi Yu, Kaohsiung (TW); Yu-Hsiang Tsai, Hsinchu County (TW); Kuan-Ting Chen, Yunlin County (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 17/106,188

(22) Filed: Nov. 30, 2020

(65) Prior Publication Data

US 2022/0013090 A1 Jan. 13, 2022

Related U.S. Application Data

(60) Provisional application No. 63/050,072, filed on Jul. 9, 2020.

(51) Int. Cl.
*G09G 5/38* (2006.01)
*G06T 7/70* (2017.01)
(Continued)

(52) U.S. Cl.
CPC .............. *G09G 5/38* (2013.01); *G01S 13/06* (2013.01); *G01S 19/01* (2013.01);
(Continued)

(58) Field of Classification Search
CPC ........ G09G 5/38; G09G 2354/00; G06T 7/50; G06T 7/70; G06T 2207/30196;
(Continued)

(56) References Cited

U.S. PATENT DOCUMENTS 10,646,283 B2 5/2020 Johnson et al.
2013/0009863 A1* 1/2013 Noda ................... G06F 3/013
345/156

(Continued)

FOREIGN PATENT DOCUMENTS

CN 107506032 12/2017
CN 107613897 1/2018
(Continued)

OTHER PUBLICATIONS

"Office Action of Taiwan Counterpart Application", dated Dec. 30, 2021, pp. 1-13.

*Primary Examiner* — Jin Ge
(74) *Attorney, Agent, or Firm* — JCIPRNET (57) ABSTRACT

A method, a processing device and a display system for information display are provided. The system includes a display being light transmissive, at least one first information extraction device, at least one second information extraction device, and a processing device. The processing device is connected to the display, the first information extraction device and the second information extraction device. The first information extraction device is configured to extract a user's position information and posture information. The second information extraction device is configured to extract a target object's position information and posture information. The processing device is configured to perform coordinate transformation according to the user's position information and posture information and the target object's position information and posture information, to generate overlay information between the user and the target object, and display related stereoscopic information of the target object on the display according to the overlay information.

19 Claims, 11 Drawing Sheets

(51) Int. Cl.
- *G06T 7/50* (2017.01)
- *G02B 27/01* (2006.01)
- *G01S 19/01* (2010.01)
- *G01S 13/06* (2006.01)
- *A61B 90/00* (2016.01)
- *A61B 34/20* (2016.01)

(52) U.S. Cl.
CPC ............ *G02B 27/0101* (2013.01); *G06T 7/50* (2017.01); *G06T 7/70* (2017.01); *A61B 2034/2051* (2016.02); *A61B 2090/372* (2016.02); *G02B 2027/014* (2013.01); *G02B 2027/0138* (2013.01); *G02B 2027/0141* (2013.01); *G06T 2207/30196* (2013.01); *G09G 2354/00* (2013.01)

(58) Field of Classification Search
CPC ..... G01S 13/06; G01S 19/01; G02B 27/0101; G02B 2027/0138; G02B 2027/0141; A61B 2034/2051; A61B 2090/372
USPC .......................................................... 345/419
See application file for complete search history.

(56) References Cited

U.S. PATENT DOCUMENTS

| | | | |
|---|---|---|---|
| 2013/0265232 A1* | 10/2013 | Yun | G06F 3/011 345/158 |
| 2014/0098088 A1* | 4/2014 | Ryu | G06T 19/006 345/419 |
| 2014/0204023 A1* | 7/2014 | Kumar | G09G 3/20 345/156 |
| 2015/0154801 A1* | 6/2015 | Lee | G06F 3/013 345/589 |
| 2016/0174934 A1* | 6/2016 | Cong | A61B 8/08 600/459 |
| 2016/0261793 A1* | 9/2016 | Sivan | H04N 19/597 |
| 2017/0119481 A1* | 5/2017 | Romo | A61B 17/00234 |
| 2018/0165857 A1* | 6/2018 | Lee | G06T 11/60 |
| 2018/0246336 A1 | 8/2018 | Greenberg | |
| 2019/0050071 A1* | 2/2019 | Liu | G06F 3/017 |
| 2019/0053851 A1 | 2/2019 | Siemionow et al. | |
| 2020/0077072 A1* | 3/2020 | Hsu | G06T 7/75 |
| 2021/0084357 A1* | 3/2021 | Tajik | H04N 21/42203 |
| 2021/0195360 A1* | 6/2021 | Leider | G06T 19/006 |

FOREIGN PATENT DOCUMENTS

| | | |
|---|---|---|
| TW | I594174 | 8/2017 |
| TW | 202009877 | 3/2020 |

* cited by examiner

METHOD, PROCESSING DEVICE, AND DISPLAY SYSTEM FOR INFORMATION DISPLAY

CROSS-REFERENCE TO RELATED APPLICATION

This application claims the priority benefit of U.S. provisional application Ser. No. 63/050,072, filed on Jul. 9, 2020. The entirety of the above-mentioned patent application is hereby incorporated by reference herein and made a part of this specification.

TECHNICAL FIELD

The disclosure relates to an information display technology.

RELATED ART

With the development of image processing technology and spatial positioning technology, the application of transparent displays has gradually received attention. In this type of technology, a display may be used in combination with a physical object, and with the help of related virtual information, an interactive experience is generated according to user needs, and information can be presented in a more intuitive way.

However, in current display systems, a user and a physical object are positioned by image recognition, and then, planar graphics data is moved through a transparent display in accordance with relative positions of the user's line of sight and the physical object. Under the premise that the postures of the user and the physical object are not considered, whether planar graphics data or stereoscopic graphics data displayed on the display is unlikely to be precisely overlaid with the physical object, and discomfort is caused to the user during viewing.

SUMMARY

The disclosure provides a method, a processing device and a display system for information display.

In one exemplary embodiment of the disclosure, the above-mentioned system includes a display being light transmissive, at least one first information extraction device, at least one second information extraction device, and a processing device. The processing device is connected to the display, the first information extraction device and the second information extraction device. The first information extraction device is configured to extract position information and posture information of a user. The second information extraction device is configured to extract position information and posture information of a target object. The processing device is configured to perform coordinate transformation according to the position information and the posture information of the user as well as the position information and the posture information of the target object, to generate overlay information between the user and the target object, and display related stereoscopic information of the target object on the display according to the overlay information.

In one exemplary embodiment of the disclosure, the above-mentioned method for information display is adapted for a display system that includes a display being light transmissive, at least one first information extraction device, at least one second information extraction device and a processing device. The method for information display includes the following. Position information and posture information of a user are extracted by the first information extraction device. Position information and posture information of a target object are extracted by the second information extraction device. Coordinate transformation is performed according to the position information and the posture information of the user as well as the position information and the posture information of the target object, to generate overlay information between the user and the target object. Related stereoscopic information of the target object is displayed on the display according to the overlay information.

In one exemplary embodiment of the disclosure, the above-mentioned processing device is connected to a display, a first information extraction device and a second information extraction device. The first information extraction device is configured to extract position information and posture information of a user, and the second information extraction device is configured to extract position information and posture information of a target object. The processing device includes a memory and a processor. The memory is configured to store data. The processor is configured to acquire the position information and the posture information of the user that are extracted by the first information extraction device; acquire the position information and the posture information of the target object that are extracted by the second information extraction device; perform coordinate transformation according to the position information and the posture information of the user as well as the position information and the posture information of the target object, to generate overlay information between the user and the target object; and display related stereoscopic information of the target object on the display according to the overlay information.

Several exemplary embodiments accompanied with figures are described in detail below to further describe the disclosure in details.

DESCRIPTION OF THE EMBODIMENTS

Some exemplary embodiments of the disclosure will be hereinafter described in detail with reference to the accompanying drawings. In the following description, the same reference numerals in different drawings are regarded as the same or similar elements. These exemplary embodiments are only a part of the disclosure and do not disclose all of the possible implementations of the disclosure. More specifically, these exemplary embodiments are only examples of the method, the device and the system within the scope of the claims of the disclosure.

Figure 1:
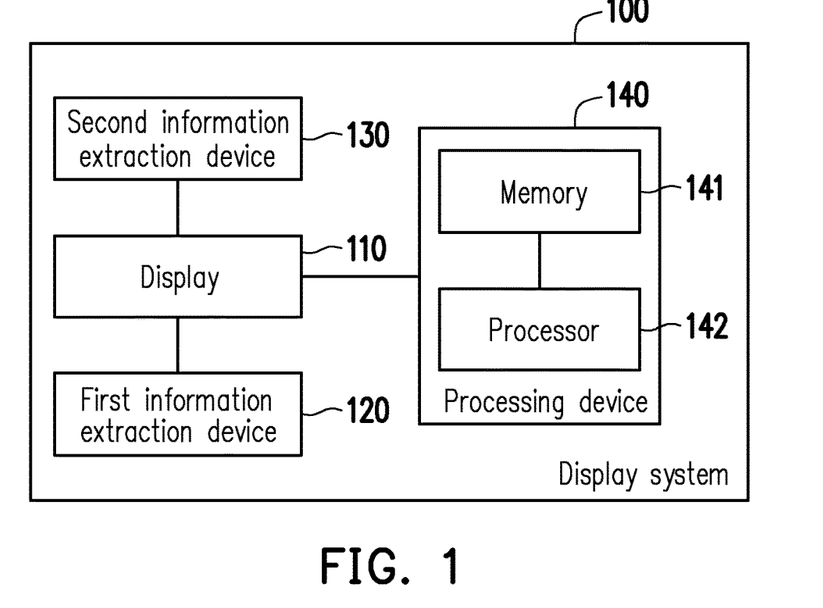
FIG. 1 is a schematic diagram of a display system according to one exemplary embodiment of the disclosure.

FIG. 1 is a schematic diagram of a display system according to one exemplary embodiment of the disclosure. First of all, FIG. 1 introduces members and configuration relationships in a system. The detailed functions will be disclosed together with reference to the flowcharts of the subsequent exemplary embodiments.

Referring to FIG. 1, a display system 100 in this exemplary embodiment includes a display 110, at least one first information extraction device 120, at least one second information extraction device 130, and a processing device 140. The processing device 140 may be wirelessly, wiredly, or electrically connected to the display 110, the first information extraction device 120, and the second information extraction device 130.

The display 110 is configured to display information, and includes, for example, a penetrating type light transmissive display such as a liquid crystal display (LCD), a field sequential color LCD display, a light emitting diode (LED) display, an electrowetting display, or a projection type light transmissive display. The content viewed by a user through the display 110 may be a physical scene overlaid with a virtual image.

The first information extraction device 120 is configured to extract position information and posture information of the user, and the second information extraction device 130 is configured to extract position information and posture information of a target object in the physical scene. The first information extraction device 120 may include, for example, at least one image sensor or at least one image sensor combined with at least one depth sensor to perform image recognition positioning on the target object. The image sensor may be a visible light sensor or an invisible light sensor such as an infrared sensor; the depth sensor may be a light field radar or an ultrasonic sensor. In addition, the first information extraction device 120 may further include, for example, an optical positioner, to perform optical spatial positioning on the user. Here, the optical positioner may include a positioner device and a positioning light ball. Generally, the positioner device may be an active device, and the positioning light ball may be a passive device. The disclosure is not limited thereto, and specific applications will be described later. That is, a device or a combination thereof falls within the scope of the first information extraction device 120 as long as it can obtain the user's position information and posture information by positioning.

The second information extraction device 120 may include, for example, at least one image sensor or at least one image sensor combined with at least one depth sensor to perform image recognition positioning on the target object, or an optical positioner to perform optical spatial positioning on the target object, or a magnetic positioner to perform electromagnetic navigation spatial positioning on the target object. In addition, in response to special scenario needs, the second information extraction device 130 may include a GPS positioner to position a target object (for example, a building, a vehicle, or a pedestrian) outside the display 110, or may include a combination of rangefinders such as a GPS positioner, a camera, and a radar, to extract position information and posture information of the target object. That is, a device or a combination thereof falls within the scope of the second information extraction device 130 as long as it can obtain the target object's position information and posture information by positioning.

Those of ordinary skill in the art should understand that the above-mentioned image sensor may be configured to capture an image and includes an imaging lens having a lens and a photosensitive element. The above-mentioned depth sensor may be configured to detect depth information, and may be separately implemented by active depth sensing technology and passive depth sensing technology. The active depth sensing technology may be used in combination with a time difference ranging technology to calculate the depth information by active emission of a source light, an infrared ray, ultrasound, laser or the like as a signal. The passive depth sensing technology may use two image sensors to capture two images in front of them respectively at different viewing angles, so as to calculate the depth information using parallax between the two images. The above-mentioned optical positioner may be disposed on a luminous body (for example, a tracking light ball) on the user and/or the target object, and be used in combination with an imaging lens or other optical detector, thereby providing spatial coordinates of the user and/or the target object. These spatial coordinates may include three-degree-of-freedom (3-DOF) information or six-degree-of-freedom (6-DOF) information. The above-mentioned magnetic positioner (for example, an electromagnetic navigation probe) may penetrate deep into the target object to obtain the spatial coordinates of the target object according to a measured physical quantity (for example, a voltage or a current).

The processing device 140 is configured to control operation of the display system 100, and includes a memory 141 and a processor 142. The memory 141 may be any type of fixed or portable random access memory (RAM), read-only memory (ROM), flash memory, hard disk or other similar device, integrated circuit or a combination thereof. The processor 142 may be, for example, a central processing unit (CPU), an application processor (AP), or other programmable general purpose or special purpose microprocessor, a digital signal processor (DSP), an image signal processor (ISP), a graphics processing unit (GPU) or other similar device, or an integrated circuit or a combination thereof.

In this exemplary embodiment, the processing device 140 may be built in the display 110. The first information extraction device 120 and the second information extraction device 130 may respectively be disposed on opposite sides of the display 110, opposite sides of a field to which the display system 100 belongs relative to the display 110, or the like, and are configured to position the user and the target object and transmit information to the processing device 140 in a wired or wireless manner through their respective communication interfaces. In another exemplary embodiment, the display system 100 may be a single integrated system, and may be implemented as a head-mounted display device, a smartphone, a tablet computer or the like. The disclosure is not limited thereto. In the following exemplary embodiments, implementation details of a method for information display will be described with reference to the elements of the display system 100.

Figure 2:
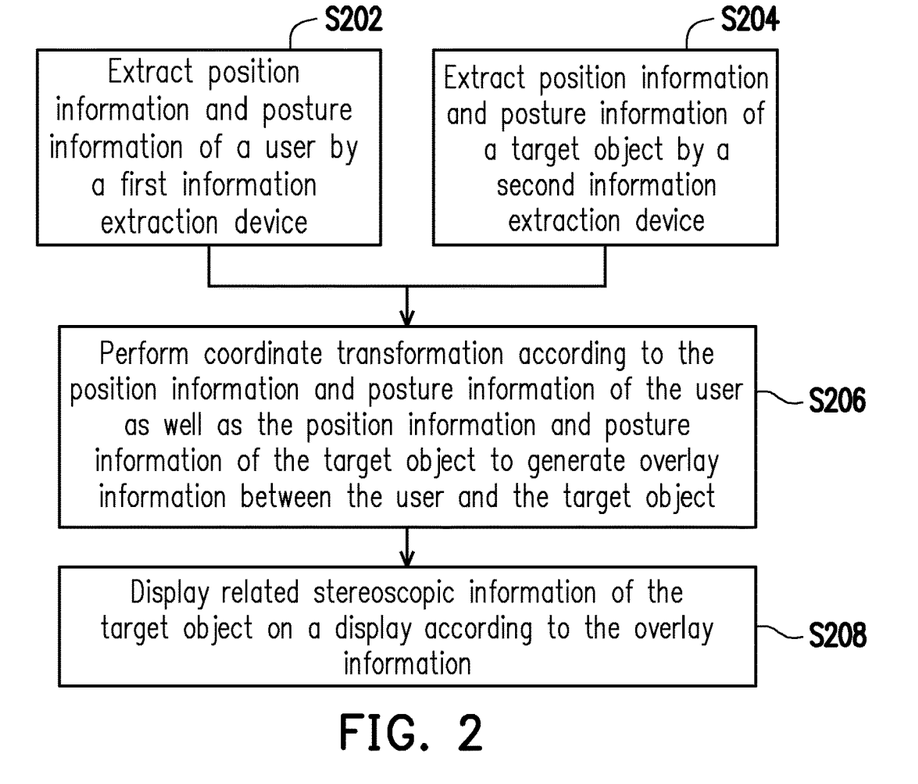
FIG. 2 is a flowchart of a method for information display according to one exemplary embodiment of the disclosure.

FIG. 2 is a flowchart of a method for information display according to one exemplary embodiment of the disclosure. The process flow of FIG. 2 may be implemented by the display system 100 of FIG. 1. Here, the user may view the target object and its related stereoscopic information through the display 110 of the display system 100.

Referring to FIG. 1 and FIG. 2 together, first of all, the processing device 140 of the display system 100 extracts position information and posture information of a user by the first information extraction device 120 (step S202), and extracts position information and posture information of a target object by the second information extraction device 130 (step S204). As described above, the first information extraction device 120 and the second information extraction device 130 are, for example, image sensors, depth sensors, optical positioners, magnetic positioners, and combinations thereof, capable of positioning the location and posture of the user and the target object. A configuration manner will be described in the subsequent exemplary embodiments.

Next, the processing device 140 performs coordinate transformation according to the position information and the posture information of the user as well as the position information and the posture information of the target object, to generate overlay information between the user and the target object (step S206). Here, the position information and the posture information of the user may include a user position coordinate and a user orientation angle of the user relative to the first information extraction device 120, and the position information and the posture information of the target object may include a target object position coordinate and a target object orientation angle of the target object relative to the second information extraction device 130. The processing device 140 may transform the user position coordinate, the user orientation angle, the target object position coordinate and the target object orientation angle to the same coordinate system (for example, a world coordinate system or a camera coordinate system). Next, the processing device 140 calculates positions and angles of the user and the target object relative to the display 110 according to the user position coordinate after transformation, the user orientation angle after transformation, the target object position coordinate after transformation and the target object orientation angle after transformation, to generate the overlay information suitable for the user to view the target object.

In one exemplary embodiment, the overlay information includes a display position, a display angle and a display size of the related stereoscopic information displayed on the display 110 when the user views the target object. Here, the related stereoscopic information may be stored in the memory 141 or be acquired from other databases through a communication interface (not shown). The display position and display angle of the related stereoscopic information presented on the display 110 are associated with a depth distance of the user relative to the display 110, a depth distance of the target object relative to the display 110, an offset angle of the user relative to a depth axis of the display 110, and an offset angle of the target object relative to the depth axis of the display 110. The display size of the related stereoscopic information on the display 110 is associated with the depth distance of the user relative to the display 110 and the depth distance of the target object relative to the display 110.

Figure 3A:
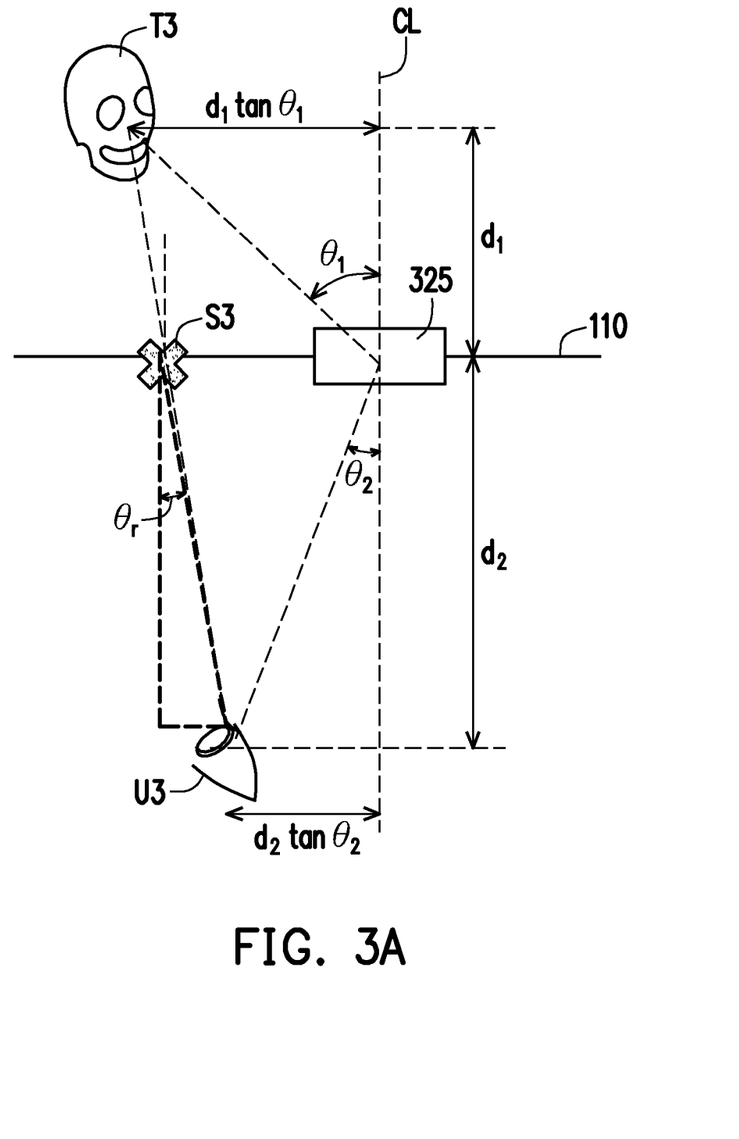
FIG. 3A and FIG. 3B are schematic diagrams of an overlay information calculation method according to one exemplary embodiment of the disclosure.
Figure 3B:
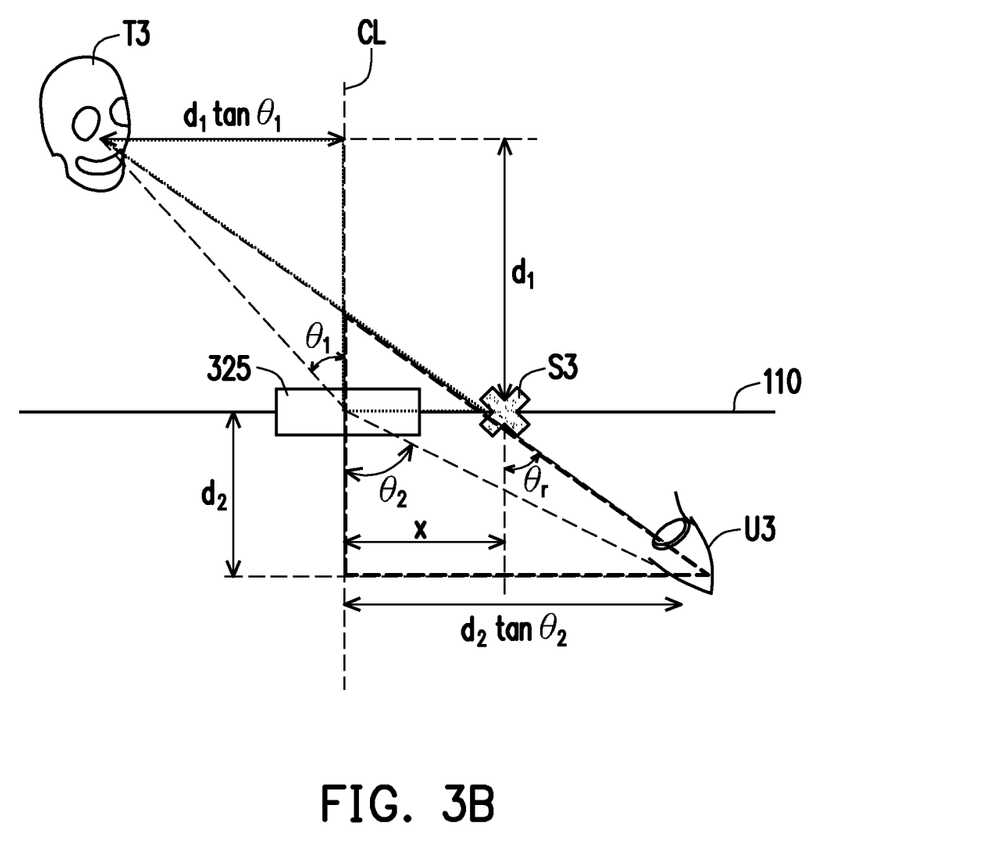

FIG. 3A and FIG. 3B are schematic diagrams of an overlay information calculation method according to one exemplary embodiment of the disclosure. To facilitate the description, here, the first information extraction device 120 and the second information extraction device 130 will be collectively referred to as a positioning system 325.

Referring first to FIG. 3A and FIG. 1 together, in this embodiment, a target object T3 and a user U3 are located on the same side of the positioning system 325. Assuming that the first information extraction device 120 and the second information extraction device 130 are implemented as camera modules including one or more image sensors, the target object T3 and the user U3 are located on the same side of a camera center point connecting line CL. It is assumed that depth distances of the target object T3 and the user U3 relative to the display 110 are respectively $d_1$ and $d_2$, and offset angles of the target object T3 and the user U3 relative to the depth axis of the display 110 are respectively $\theta_1$ and $\theta_2$. Accordingly, the processing device 140 may display offset amounts of position coordinates (u,v) of related stereoscopic information S3 of the target object T3 on a plane u axis and a vertical v axis of the display 110 according to the overlay information calculated by equations (1.1) to (1.3):

$$x = \frac{d_2\tan\theta_2 * d_1 + d_1\tan\theta_1 * d_2}{d_1 + d_2} \quad (1.1)$$

$$\theta_{rx} = \tan^{-1}\left|\frac{|d_2\tan\theta_2 - x|}{d_2}\right| \quad (1.2)$$

$$R(z) = \frac{d2}{d1 + d2} \quad (1.3)$$

in which x is an offset amount of the related stereoscopic information S3 on the plane u axis of the display 110, $\theta_{rx}$ is an orientation angle of the related stereoscopic information S3 on the plane u axis of the display 110, and R (z) is a scaling ratio of the related stereoscopic information S3. In addition, an offset amount y and an orientation angle $\theta_{ry}$ of the related stereoscopic information S3 on the vertical v axis of the display 110 can also be calculated in a similar manner. The scaling ratio here may be a scaling ratio relative to the original size of the related stereoscopic information, and is adjusted according to a relative distance relationship between the user U3 and the target object T3.

Referring again to FIG. 3B and FIG. 1 together, in this embodiment, the target object T3 and the user U3 are located on different sides of the positioning system 325. Assuming that the first information extraction device 120 and the second information extraction device 130 are implemented as camera modules including one or more image sensors, the target object T3 and the user U3 are located on different sides of the camera center point connecting line CL. Accordingly, the processing device 140 may display the offset amounts of the position coordinates (u,v) of the related stereoscopic information S3 of the target object T3 on the plane u axis and the vertical v axis of the display 110 according to the overlay information calculated by equations (2.1) to (2.3):

$$x = \frac{d_1 d_2(\tan\theta_2 - \tan\theta_1)}{d_1 + d_2} \quad (2.1)$$

$$\theta_{rx} = \tan^{-1}\left|\frac{d_1 d_2\tan\theta_1 + d_2^2\tan\theta_2}{d_1 d_2 + d_2^2}\right| \quad (2.2)$$

$$R(z) = \frac{d2}{d1 + d2} \quad (2.3)$$

in which x is the offset amount of the related stereoscopic information S3 on the plane u axis of the display 110, $\theta_{rx}$ is the orientation angle of the related stereoscopic information S3 on the plane u axis of the display 110, and R(z) is the scaling ratio of the related stereoscopic information S3. In addition, the offset amount y and the orientation angle $\theta_{ry}$ of the related stereoscopic information S3 on the vertical v axis of the display 110 can also be calculated in a similar manner.

Referring back to FIG. 2, the processing device 140 displays the related stereoscopic information of the target object on the display 110 according to the generated overlay information (step S208). In this way, whether the user views the display 110 in any position, orientation, or posture, the processing device 140 can automatically and adaptively adjust the display position, the display angle and the display size of the related stereoscopic information on the display 110, so as to realize display of multi-angle related stereoscopic information.

To facilitate understanding, in the following embodiments, use scenarios and details of the process of FIG. 2 will be described with reference to different configurations of the display system 100.

Figure 4A:
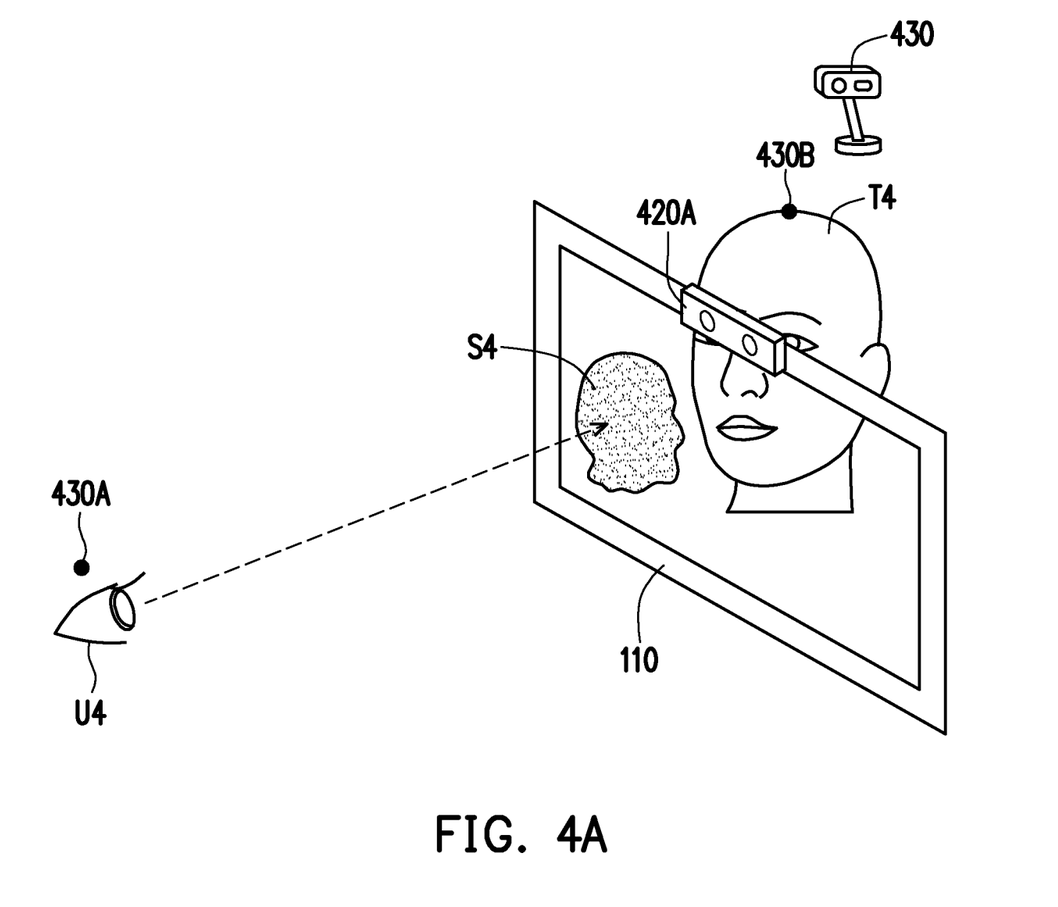
FIG. 4A is a schematic diagram of an application scenario of a display system according to one exemplary embodiment of the disclosure.
Figure 4B:
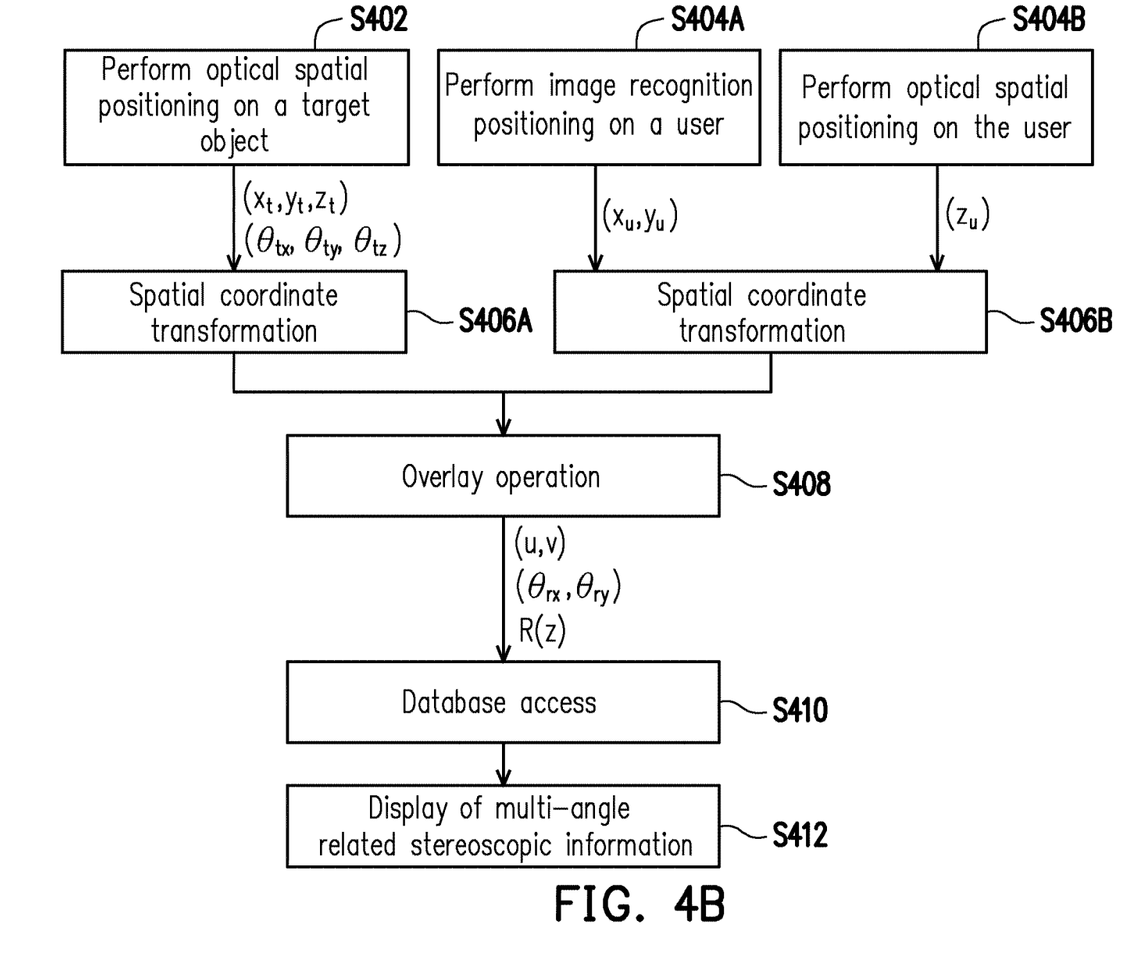
FIG. 4B is a flowchart of a method for information display according to one exemplary embodiment of the disclosure.

FIG. 4A is a schematic diagram of an application scenario of a display system according to one exemplary embodiment of the disclosure. FIG. 4B is a flowchart of a method for information display according to one exemplary embodiment of the disclosure. In this exemplary embodiment, the first information extraction device 120 is implemented as a camera module including one or more image sensors and an optical positioner, and the second information extraction device 130 is implemented as an optical positioner.

Referring first to FIG. 1, FIG. 4A and FIG. 4B, in this exemplary embodiment, the processing device 140 of the display system 100 performs optical spatial positioning on a target object T4 by an optical positioner 430 and a positioning light ball 430B placed on the target object T4 (step S402), and acquires position information $(x_t, y_t, z_t)$ and posture information $(\theta_{tx}, \theta_{ty}, \theta_{tz})$ of the target object T4. In addition, the processing device 140 performs image recognition positioning on a user U4 by a camera module 420A (step S404A), and performs optical spatial positioning on the user U4 by the optical positioner 430 and a positioning light ball 430A placed on the user U4 (step S404B), so as to generate plane position information $(x_u, y_u)$ and depth position information $(z_u)$, respectively, of the user U4.

Next, the processing device 140 performs spatial coordinate transformation respectively on the position information $(x_t, y_t, z_t)$ and posture information $(\theta_{tx}, \theta_{ty}, \theta_{tz})$ of the target object T4 and the position information $(x_u, y_u, z_u)$ of the user U4 (steps S406A and S406B) to transform the information to the same coordinate system, and then performs an overlay operation between the target object T4 and the user U4 (step S408), so as to generate overlay information (that is, position information (u,v), orientation angle $(\theta_{rx}, \theta_{ry})$, and scaling ratio R(z)). Next, the processing device 140 performs database access (step S410), to acquire the related stereoscopic information of the target object T4 from a database, and displays multi-angle related stereoscopic information S4 according to the overlay information (step S412). In addition, when the user U4 moves to another position, the process will return to steps S404A and S404B to recalculate different overlay information, and the user U4 will view the related stereoscopic information in different positions, different orientation angles, and different sizes on the display 110.

Figure 5A:
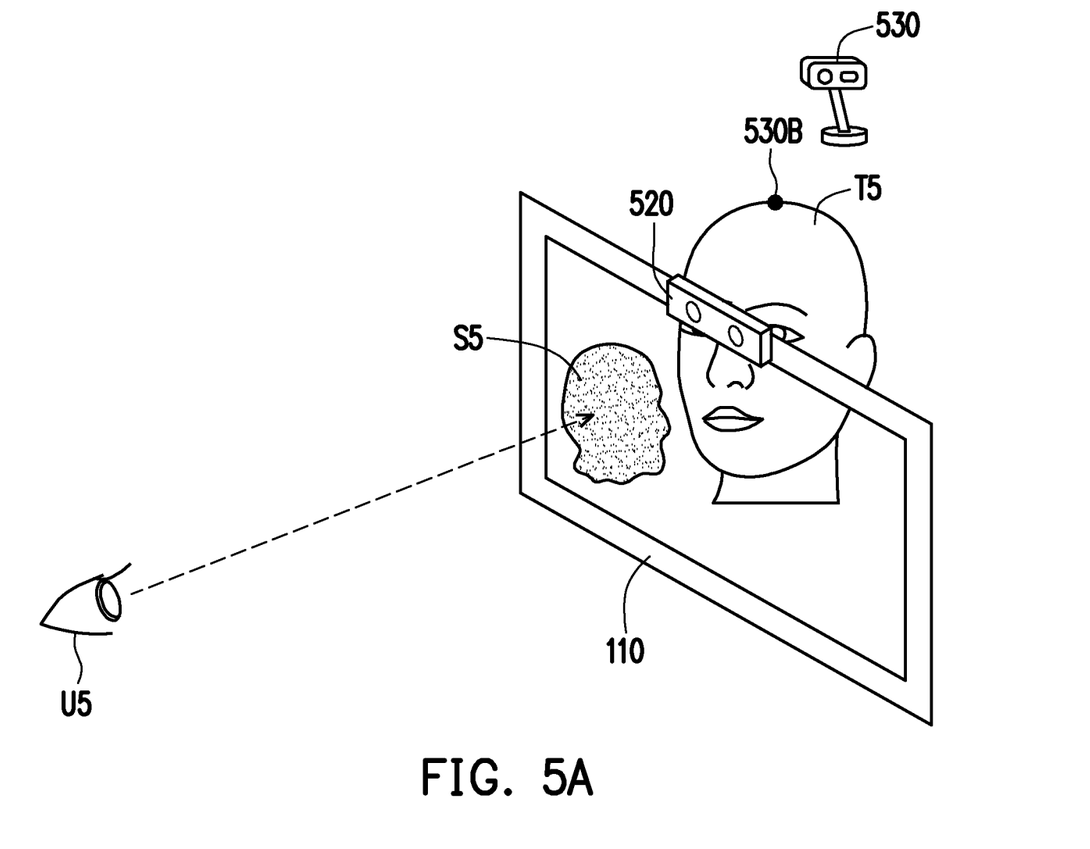
FIG. 5A is a schematic diagram of an application scenario of a display system according to one exemplary embodiment of the disclosure.
Figure 5B:
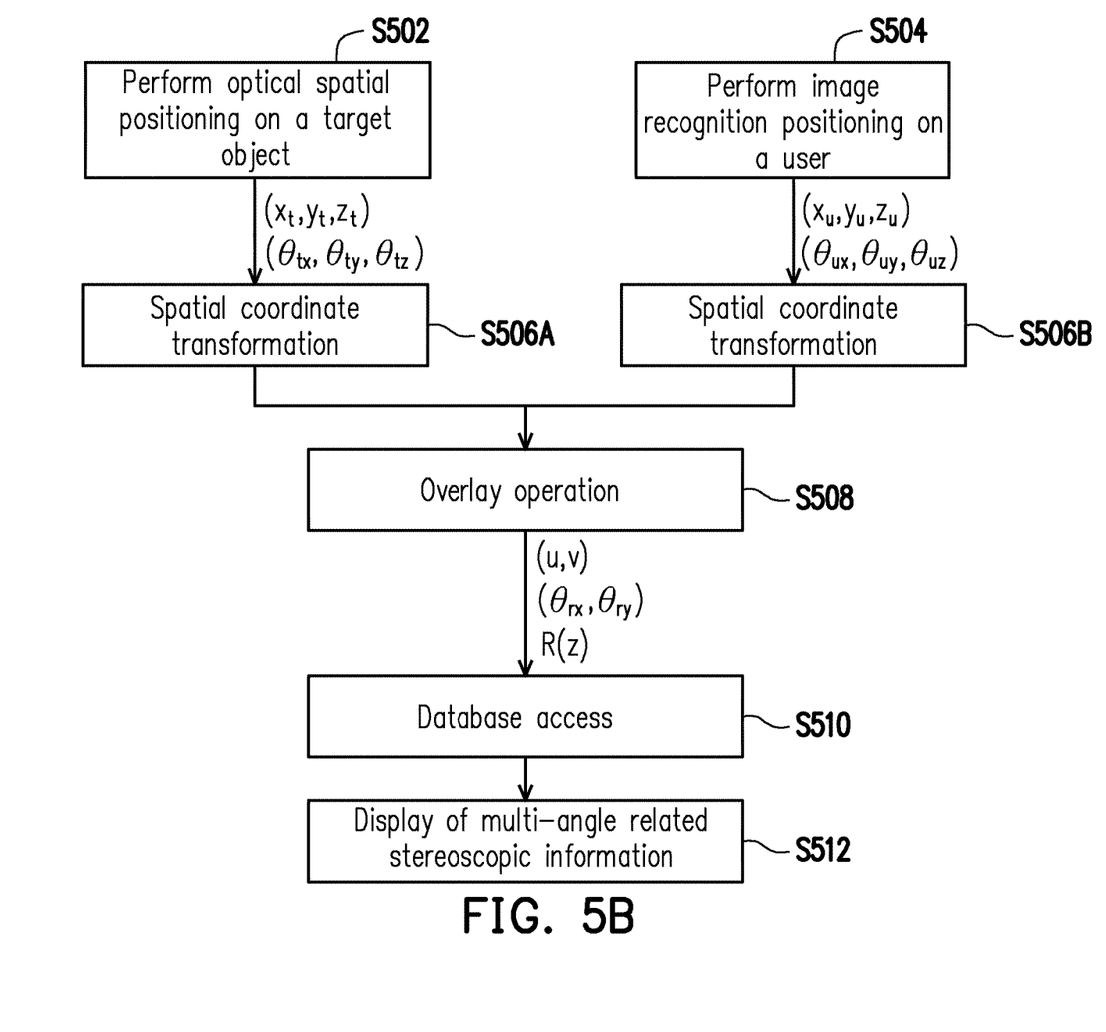
FIG. 5B is a flowchart of a method for information display according to one exemplary embodiment of the disclosure.

FIG. 5A is a schematic diagram of an application scenario of a display system according to one exemplary embodiment of the disclosure. FIG. 5B is a flowchart of a method for information display according to one exemplary embodiment of the disclosure. In this exemplary embodiment, the first information extraction device 120 is implemented as a camera module, and the second information extraction device 130 is implemented as an optical positioner.

Referring first to FIG. 1, FIG. 5A and FIG. 5B, in this exemplary embodiment, the processing device 140 of the display system 100 performs optical spatial positioning on a target object T5 by an optical positioner 530 and a positioning light ball 530B placed on the target object T5 (step S502), and acquires the position information $(x_t, y_t, z_t)$ and posture information $(\theta_{tx}, \theta_{ty}, \theta_{tz})$ of the target object T5. In addition, the processing device 140 performs image recognition positioning on a user U5 by a camera module 520 (step S504) to generate position information $(x_u, y_u, z_u)$ and posture information $(\theta_{ux}, \theta_{uy}, \theta_{uz})$ of the user U5. In addition, those of ordinary skill in the art should understand that, according to an image of the user U5, the processing device 140 may determine the user's viewing angle and direction according to the user's eye position and a rotation range of the user's face, and accordingly calculates the posture information of the user U5.

Next, the processing device 140 performs spatial coordinate transformation respectively on the position information $(x_t, y_t, z_t)$ and posture information $(\theta_{tx}, \theta_{ty}, \theta_{tz})$ of the target object T5 as well as the position information $(x_u, y_u, z_u)$ and posture information $(\theta_{ux}, \theta_{uy}, \theta_{uz})$ of the user U5 (steps S506A and S506B) to transform the information to the same coordinate system, and then performs an overlay operation between the target object T5 and the user U5 (step S508), so as to generate the overlay information (that is, position information (u,v), orientation angle $(\theta_{rx}, \theta_{ry})$, and scaling ratio R(z)). Next, the processing device 140 performs database access (step S510), to acquire the related stereoscopic information of the target object T5 from a database, and displays multi-angle related stereoscopic information S5 according to the overlay information (step S512).

Figure 6A:
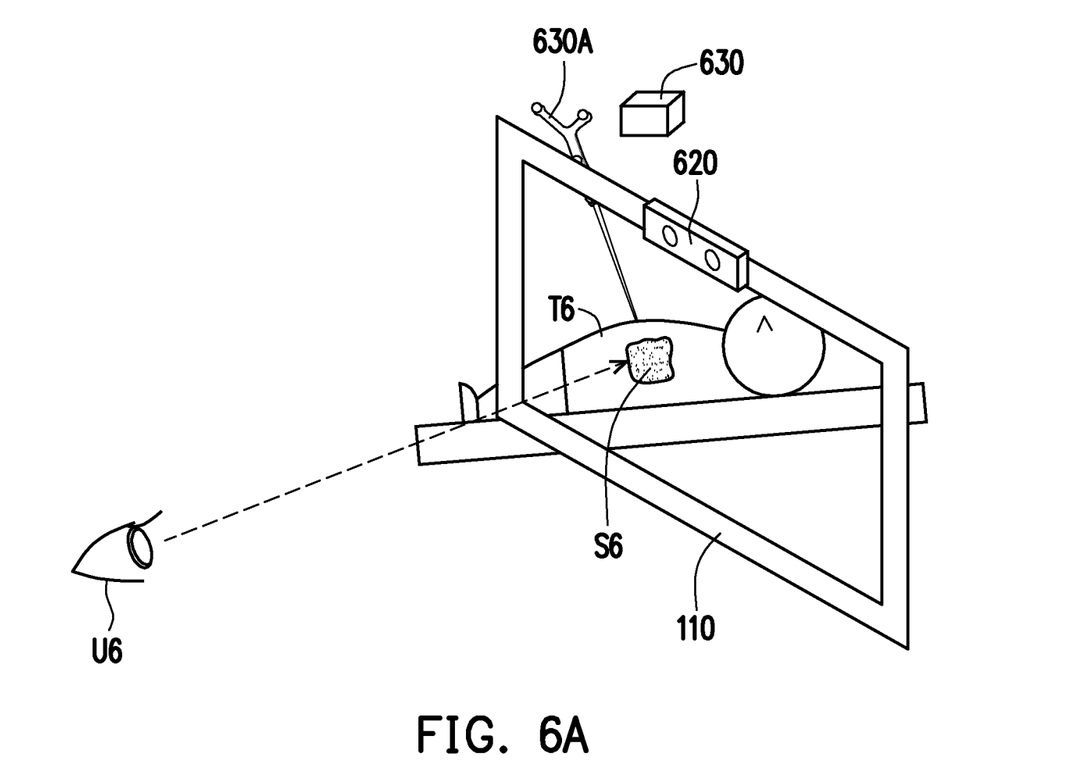
FIG. 6A is a schematic diagram of an application scenario of a display system according to one exemplary embodiment of the disclosure.
Figure 6B:
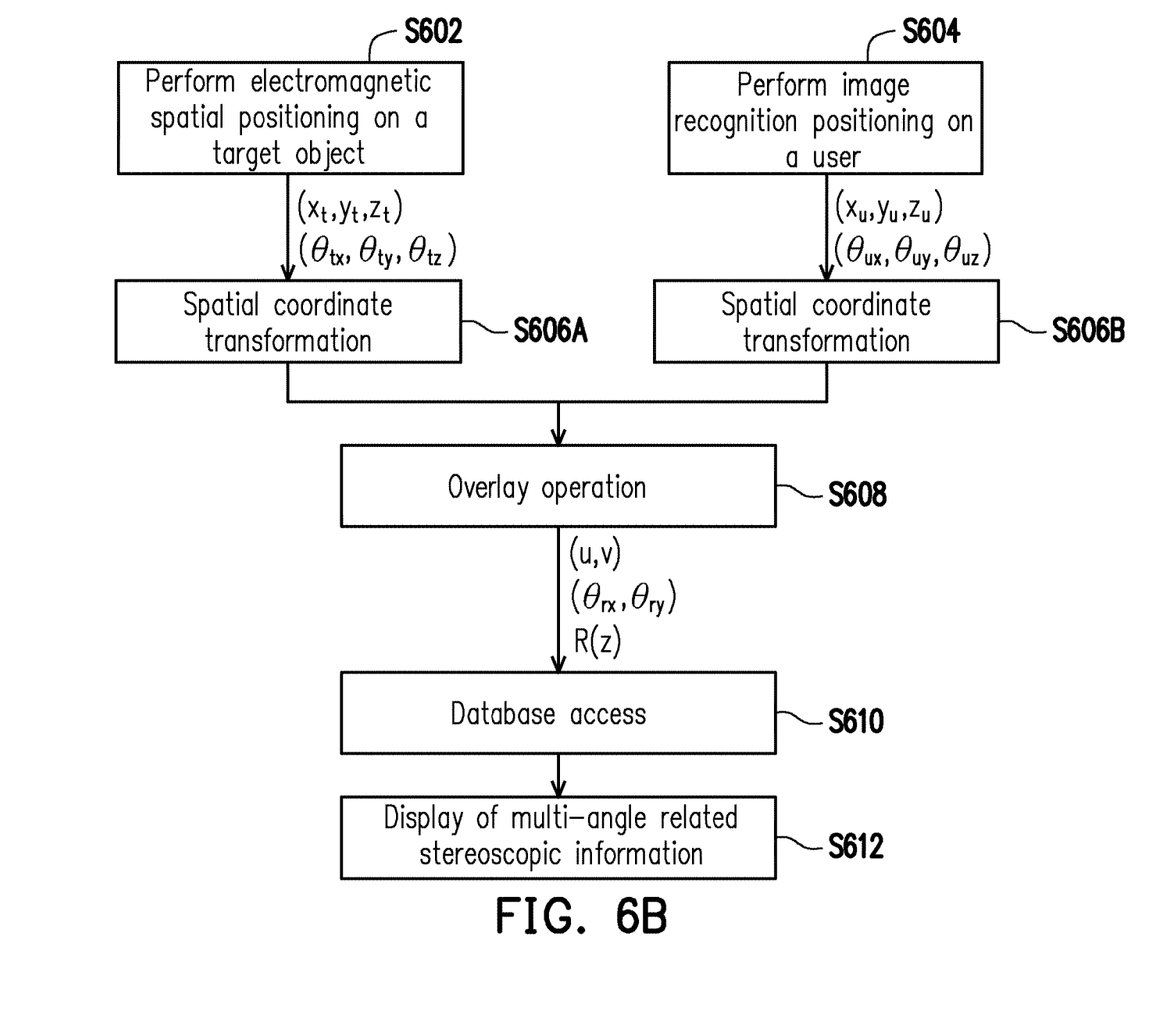
FIG. 6B is a flowchart of a method for information display according to one exemplary embodiment of the disclosure.

FIG. 6A is a schematic diagram of an application scenario of a display system according to one exemplary embodiment of the disclosure. FIG. 6B is a flowchart of a method for information display according to one exemplary embodiment of the disclosure. In this exemplary embodiment, the first information extraction device 120 is implemented as a camera module, and the second information extraction device 130 is implemented as an electromagnetic navigation spatial positioning system.

Referring first to FIG. 1, FIG. 6A and FIG. 6B, in this exemplary embodiment, the processing device 140 of the display system 100 performs electromagnetic spatial positioning on a target object T6 by an electromagnetic navigation spatial positioning system 630 and an electromagnetic navigation probe 630A (step S602), and acquires the position information $(x_t, y_t, z_t)$ and posture information $(\theta_{tx}, \theta_{ty}, \theta_{tz})$ of the target object T6. In this exemplary embodiment, the electromagnetic navigation probe 630A may enter the target object T6, for example, as a surgical aid. In addition, the processing device 140 performs image recognition positioning on a user U6 by a camera module 620 (step S604) to generate position information $(x_u, y_u, z_u)$ and posture information $(\theta_{ux}, \theta_{uy}, \theta_{uz})$ of the user U6.

Next, the processing device 140 performs spatial coordinate transformation respectively on the position information $(x_t, y_t, z_t)$ and posture information $(\theta_{tx}, \theta_{ty}, \theta_{tz})$ of the target object T6 as well as the position information $(x_u, y_u, z_u)$ and posture information $(\theta_{ux}, \theta_{uy}, \theta_{uz})$ of the user U6 (steps S606A and S606B) to transform the information to the same coordinate system, and then performs an overlay operation between the target object T6 and the user U6 (step S508), so as to generate the overlay information (that is, position information (u,v), orientation angle ($\theta_{rx},\theta_{ry}$), and scaling ratio R(z)). Next, the processing device 140 performs database access (step S610), to acquire the related stereoscopic information of the target object T6 from a database, and displays multi-angle related stereoscopic information S6 according to the overlay information (step S612).

Figure 7A:
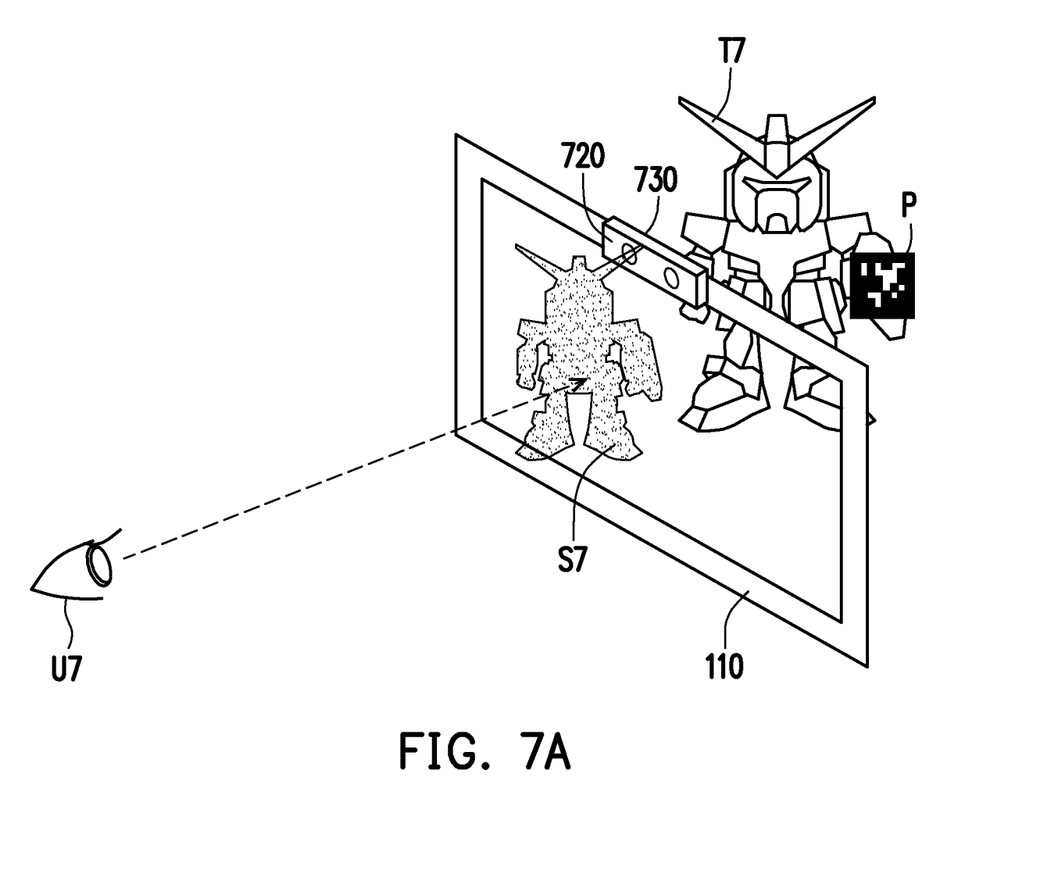
FIG. 7A is a schematic diagram of an application scenario of a display system according to one exemplary embodiment of the disclosure.
Figure 7B:
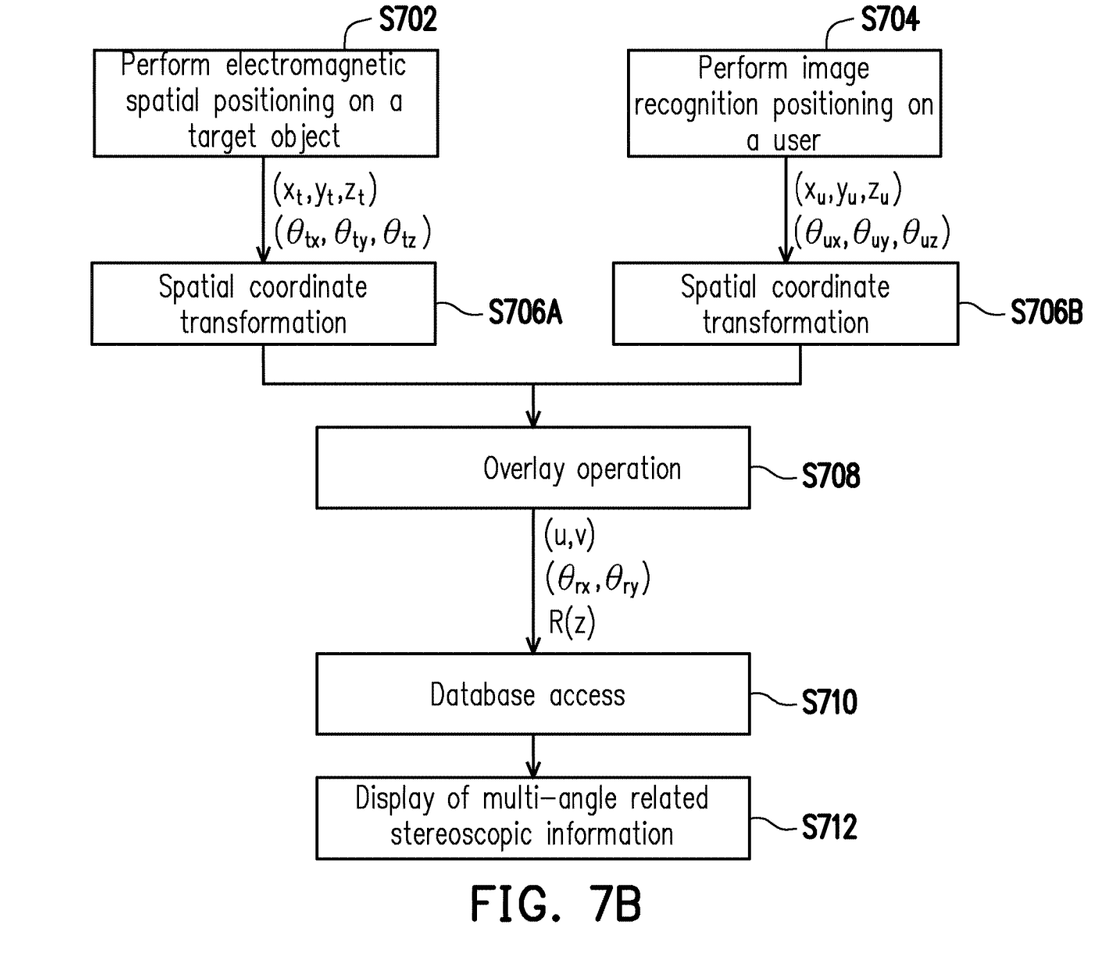
FIG. 7B is a flowchart of a method for information display according to one exemplary embodiment of the disclosure.

FIG. 7A is a schematic diagram of an application scenario of a display system according to one exemplary embodiment of the disclosure. FIG. 7B is a flowchart of a method for information display according to one exemplary embodiment of the disclosure. In this exemplary embodiment, the first information extraction device 120 and the second information extraction device 130 are implemented as camera modules.

Referring first to FIG. 1, FIG. 7A and FIG. 7B, in this exemplary embodiment, the processing device 140 of the display system 100 performs image recognition positioning on a target object T7 by a camera module 730 (step S702), and acquires the position information ($x_t,y_t,z_t$) and posture information ($\theta_{tx},\theta_{ty},\theta_{tz}$) of the target object T7. To facilitate the operation, here, a predetermined pattern P (for example, a two-dimensional barcode) may be placed on the target object T7. The processing device 140 may extract different distributions, deformations or the like of the predetermined pattern by the camera module 730 and estimate the position and posture of the target object T7. In addition, the processing device 140 performs image recognition positioning on a user U7 by a camera module 720 (step S704) to generate position information ($x_u,y_u,z_u$) and posture information ($\theta_{ux},\theta_{uy},\theta_{uz}$) of the user U7.

Next, the processing device 140 performs spatial coordinate transformation respectively on the position information ($x_t,y_t,z_t$) and posture information ($\theta_{tx},\theta_{ty},\theta_{tz}$) of the target object T7 as well as the position information ($x_u,y_u,z_u$) and posture information ($\theta_{ux},\theta_{uy},\theta_{uz}$) of the user U7 (steps S706A and S706B) to transform the information to the same coordinate system, and then performs an overlay operation between the target object T7 and the user U7 (step S708), so as to generate the overlay information (that is, position information (u,v), orientation angle ($\theta_{rx},\theta_{ry}$), and scaling ratio R(z)). Next, the processing device 140 performs database access (step S710), to acquire the related stereoscopic information of the target object T7 from a database, and displays multi-angle related stereoscopic information S7 according to the overlay information (step S712).

In the method, the processing device and the display system for information display as proposed in the exemplary embodiments of the disclosure, the coordinate transformation is performed using the position information and posture information of both the target object and the user, and the overlay information between the target object and the user is calculated, thereby realizing display of multi-angle overlaid images. Thereby, the accuracy of overlaying virtual information onto a real object is improved. The disclosure is applicable to various technologies that require overlay of image or graphics data, such as those for medical surgery, education and entertainment purposes, mobile vehicles, educational fields or the like.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A display system, comprising:
a display being light transmissive;
at least one first information extraction device, configured to extract position information and posture information of a user;
at least one second information extraction device, configured to extract position information and posture information of a target object; and
a processing device, connected to the display, the first information extraction device and the second information extraction device, and configured to:
perform coordinate transformation according to the position information and the posture information of the user as well as the position information and the posture information of the target object, to generate overlay information between the user and the target object; and
display related stereoscopic information of the target object on the display according to the overlay information, wherein the overlay information comprising a display angle of the related stereoscopic information on the display which is associated with a depth distance of the user relative to the display, a depth distance of the target object relative to the display, an offset angle of the user relative to a depth axis of the display, and an offset angle of the target object relative to the depth axis of the display.

2. The display system according to claim 1, wherein:
the position information and the posture information of the user comprise a user position coordinate and a user orientation angle of the user relative to the first information extraction device, the position information and the posture information of the target object comprise a target object position coordinate and a target object orientation angle of the target object relative to the second information extraction device; and
the processing device transforms the user position coordinate, the user orientation angle, the target object position coordinate and the target object orientation angle to a same coordinate system.

3. The display system according to claim 2, wherein:
the processing device calculates positions and angles of the user and the target object relative to the display according to the user position coordinate after transformation, the user orientation angle after transformation, the target object position coordinate after transformation and the target object orientation angle after transformation, to generate the overlay information.

4. The display system according to claim 1, wherein:
the overlay information further comprises a display position and a display size of the related stereoscopic information on the display when the user views the target object.

5. The display system according to claim 4, wherein:
the display position of the related stereoscopic information on the display is associated with a depth distance of the user relative to the display, a depth distance of the target object relative to the display, an offset angle of the user relative to a depth axis of the display, and an offset angle of the target object relative to the depth axis of the display.

6. The display system according to claim 4, wherein:
the display size of the related stereoscopic information on the display is associated with a relative distance between the user and the target object.

7. The display system according to claim 1, wherein:
the first information extraction device comprises at least one image sensor and a first optical positioner, and the second information extraction device comprises a second optical positioner;
the processing device acquires plane position information of the user by the image sensor and acquires depth position information of the user by the first optical positioner;
the processing device acquires the position information and the posture information of the target object by the second optical positioner; and
the processing device performs coordinate transformation according to the plane position information of the user, the depth position information of the user, the position information of the target object and the posture information of the target object, to generate the overlay information.

8. The display system according to claim 7, wherein:
the user and the target object respectively have thereon a first positioning light ball and a second positioning light ball, wherein the processing device acquires the depth position information of the user by the first positioning light ball through the first optical positioner, and the second optical positioner acquires the position information and the posture information of the target object according to the second positioning light ball.

9. The display system according to claim 1, wherein:
the first information extraction device comprises at least one image sensor, and the second information extraction device comprises an optical positioner;
the processing device acquires the position information and the posture information of the user by the image sensor;
the processing device acquires the position information and the posture information of the target object by the optical positioner; and
the processing device performs coordinate transformation according to the position information and the posture information of the user as well as the position information and the posture information of the target object, to generate the overlay information.

10. The display system according to claim 9, wherein:
the target object has thereon a positioning light ball, wherein the processing device acquires the position information and the posture information of the target object by the positioning light ball through the optical positioner.

11. The display system according to claim 1, wherein:
the first information extraction device comprises at least one image sensor, and the second information extraction device comprises a magnetic positioner;
the processing device acquires the position information and the posture information of the user by the image sensor;
the processing device acquires the position information and the posture information of the target object by the magnetic positioner; and
the processing device performs coordinate transformation according to the position information and the posture information of the user as well as the position information and the posture information of the target object, to generate the overlay information.

12. The display system according to claim 11, wherein:
the magnetic positioner comprises an electromagnetic navigation probe and an electromagnetic navigation spatial positioning system, wherein the processing device acquires the position information and the posture information of the target object by the electromagnetic navigation probe through the electromagnetic navigation spatial positioning system.

13. The display system according to claim 12, wherein:
the electromagnetic navigation probe is able to enter the target object.

14. The display system according to claim 1, wherein:
the first information extraction device comprises at least one first image sensor, and the second information extraction device comprises at least one second image sensor;
the processing device acquires the position information and the posture information of the user by the first image sensor;
the processing device acquires the position information and the posture information of the target object by the second image sensor; and
the processing device performs coordinate transformation according to the position information and the posture information of the user as well as the position information and the posture information of the target object, to generate the overlay information.

15. The display system according to claim 14, wherein:
the target object further comprises thereon a predetermined pattern; and
the processing device calculates the position information and the posture information of the target object according to the predetermined pattern extracted by the second image sensor.

16. The display system according to claim 1, wherein:
the second information extraction device comprises a GPS positioner configured to position the target object; and
the processing device acquires the position information and the posture information of the target object by the GPS positioner.

17. The display system according to claim 1, wherein:
the second information extraction device comprises a radar rangefinder configured to position the target object; and
the processing device acquires the position information and the posture information of the target object by the radar rangefinder.

18. A method for information display, wherein the method is adapted for a display system comprising a display being light transmissive, at least one first information extraction device, at least one second information extraction device and a processing device, wherein the method comprises:
extracting position information and posture information of a user by the first information extraction device;
extracting position information and posture information of a target object by the second information extraction device;
performing coordinate transformation according to the position information and the posture information of the user as well as the position information and the posture information of the target object, to generate overlay information between the user and the target object; and
displaying related stereoscopic information of the target object on the display according to the overlay information, wherein the overlay information comprising a display angle of the related stereoscopic information on the display which is associated with a depth distance of the user relative to the display, a depth distance of the target object relative to the display, an offset angle of the user relative to a depth axis of the display, and an offset angle of the target object relative to the depth axis of the display.

19. A processing device, wherein the processing device is connected to a display being light transmissive, at least one first information extraction device and at least one second information extraction device, wherein the first information extraction device is configured to extract position information and posture information of a user, the second information extraction device is configured to extract position information and posture information of a target object, and the processing device comprises:
  a memory, configured to store data; and
  a processor, configured to:
    acquire the position information and the posture information of the user that are extracted by the first information extraction device;
    acquire the position information and the posture information of the target object that are extracted by the second information extraction device;
    perform coordinate transformation according to the position information and the posture information of the user as well as the position information and the posture information of the target object, to generate overlay information between the user and the target object; and
    display related stereoscopic information of the target object on the display according to the overlay information, wherein the overlay information comprising a display angle of the related stereoscopic information on the display which is associated with a depth distance of the user relative to the display, a depth distance of the target object relative to the display, an offset angle of the user relative to a depth axis of the display, and an offset angle of the target object relative to the depth axis of the display.

* * * * *